(12) United States Patent
Graham et al.

(10) Patent No.: US 7,229,543 B2
(45) Date of Patent: *Jun. 12, 2007

(54) APPARATUS FOR CONTROLLING AND/OR MEASURING ADDITIVE CONCENTRATION IN AN ELECTROPLATING BATH

(75) Inventors: Lyndon W. Graham, Kalispell, MT (US); Thomas C. Taylor, Kalispell, MT (US); Thomas L. Ritzdorf, Bigfork, MT (US); Fredrick A. Lindberg, Hungry Horse, MT (US); Bradley C. Carpenter, Austin, TX (US)

(73) Assignee: Semitool, Inc., Kalispell, MT (US)

( * ) Notice: Subject to any disclaimer, the term of this patent is extended or adjusted under 35 U.S.C. 154(b) by 585 days.

This patent is subject to a terminal disclaimer.

(21) Appl. No.: 10/372,955

(22) Filed: Feb. 26, 2003

(65) Prior Publication Data

US 2003/0173224 A1 Sep. 18, 2003

Related U.S. Application Data

(60) Continuation of application No. 09/572,603, filed on May 17, 2000, now Pat. No. 6,551,479, which is a division of application No. 09/387,084, which is a continuation of application No. PCT/US99/09659, filed on May 3, 1999, now Pat. No. 6,365,033.

(60) Provisional application No. 60/083,882, filed on May 1, 1998.

(51) Int. Cl.
*C25D 21/12* (2006.01)
*G01F 1/64* (2006.01)
*G01N 27/26* (2006.01)
*G01N 27/42* (2006.01)

(52) U.S. Cl. .................. 205/83; 205/794; 204/434

(58) Field of Classification Search .................. 205/81, 205/82, 83, 793.5, 794; 204/434, 400
See application file for complete search history.

(56) References Cited

U.S. PATENT DOCUMENTS 3,649,509 A 3/1972 Morawetz et al.

(Continued)

FOREIGN PATENT DOCUMENTS

| JP | 10-060693 A | * | 3/1998 |
| JP | 10-60693 A | * | 3/1998 |

OTHER PUBLICATIONS

CAPLUS abstract of Vyakhirev ('Polarographic control of electrolyte baths. III, Zavodskaya Laboratoriya (1947), 13, 1167-71)*

(Continued)

*Primary Examiner*—Alex Noguerola
(74) *Attorney, Agent, or Firm*—Edell Shapiro & Finnan, LLC

(57) ABSTRACT

A method for measuring a target constituent of an electroplating solution using an electroanalytical technique is set forth in which the electroplating solution includes one or more constituents whose by-products skew an initial electrical response to an energy input of the electroanalytical technique. The method comprises a first step in which an electroanalytical measurement cycle of the target constituent is initiated by providing an energy input to a pair of electrodes disposed in the electroplating solution. The energy input to the pair of electrodes is provided for at least a predetermined time period corresponding to a time period in which the electroanalytical measurement cycle reaches a steady-state condition. In a subsequent step, an electroanalytical measurement of the energy output of the electroanalytical technique is taken after the electroanalytical measurement cycle has reached the steady-state condition. The electroanalytical measurement is then used to determine an amount of the target constituent in the electroplating solution. An automatic dosing system that includes the foregoing method and/or one or more known electroanalytical techniques in a close-loop system is also set forth.

32 Claims, 4 Drawing Sheets

U.S. PATENT DOCUMENTS

| | | | |
|---|---|---|---|
| 3,878,066 A | | 4/1975 | Dettke et al. |
| 3,904,493 A | | 9/1975 | Losi et al. |
| 4,051,001 A | | 9/1977 | Inoue et al. |
| 4,055,751 A | | 10/1977 | Bussman et al. |
| 4,090,926 A | | 5/1978 | Matson |
| 4,132,605 A | * | 1/1979 | Tench et al. ............... 205/787 |
| 4,146,437 A | | 3/1979 | O'Keefe |
| 4,229,218 A | | 10/1980 | Gulla et al. |
| 4,290,856 A | | 9/1981 | Inoue |
| 4,324,589 A | | 4/1982 | Gulla et al. |
| 4,326,940 A | | 4/1982 | Eckles et al. |
| 4,468,305 A | | 8/1984 | Hillis |
| 4,469,564 A | | 9/1984 | Okinaka et al. |
| 4,479,852 A | | 10/1984 | Bindra et al. |
| 4,511,443 A | | 4/1985 | Goffman et al. |
| 4,541,902 A | | 9/1985 | Kinoshita et al. |
| 4,699,081 A | | 10/1987 | Mack |
| 4,834,842 A | | 5/1989 | Langner et al. |
| 4,886,590 A | | 12/1989 | Tittle |
| 4,895,739 A | | 1/1990 | Bladon |
| 4,917,774 A | | 4/1990 | Fisher |
| 4,917,777 A | | 4/1990 | Fisher |
| 4,948,473 A | | 8/1990 | Phillippi |
| 4,952,286 A | | 8/1990 | Bladon et al. |
| 5,007,990 A | | 4/1991 | Bladon |
| 5,192,403 A | | 3/1993 | Chang et al. |
| 5,196,096 A | | 3/1993 | Chang et al. |
| 5,223,118 A | | 6/1993 | Sonnenberg et al. |
| 5,234,573 A | | 8/1993 | Takami |
| 5,364,510 A | | 11/1994 | Carpio |
| 5,368,715 A | | 11/1994 | Hurley et al. |
| 5,389,215 A | | 2/1995 | Horiuchi et al. |
| 5,391,271 A | | 2/1995 | Ludwig |
| 5,450,870 A | * | 9/1995 | Suga et al. ............... 137/3 |
| 5,484,626 A | | 1/1996 | Storjohann et al. |
| 5,534,128 A | | 7/1996 | Aso et al. |
| 5,709,839 A | * | 1/1998 | Dobson ............... 422/81 |
| 5,935,402 A | | 8/1999 | Fanti |
| 5,972,192 A | * | 10/1999 | Dubin et al. ............... 205/101 |
| 6,024,856 A | | 2/2000 | Haydu et al. |
| 6,113,769 A | | 9/2000 | Uzoh et al. |
| 6,224,737 B1 | * | 5/2001 | Tsai et al. ............... 205/123 |
| 6,254,760 B1 | | 7/2001 | Shen et al. |
| 6,280,602 B1 | | 8/2001 | Robertson |
| 6,365,033 B1 | | 4/2002 | Graham et al. |
| 6,458,262 B1 | | 10/2002 | Reid |
| 6,471,845 B1 | | 10/2002 | Dukovic et al. |

OTHER PUBLICATIONS

CAPUS abstract of Korshunov et al. ("Polarographic analysis of zinc-plating baths," Zavodskaya Laboratoriya (1947), 13, 1172-3).*

"Polarographic and Ancillary Instrumentation—303A Static Mercury Drop Electrode" product description from Princeton Applied Research downloaded Mar. 4, 2006 from www.princetonappliedresearch.com.*

Derwent abstract of JP 10-60693 A.*

JPO computer translation of Mitsuaki et al. (JP 10-060693 A).*

Z. Sun et al., *Optimized Bath Control for Void-Free Copper Deposition*, Solid State Technology, pp. 1-10, Nov. 2001.

Dennis Tench and John White, *Cyclic Pulse Voltammetric Stripping Analysis of Acid Copper Plating Baths*, Journal of the Electromechanical Society, vol. 132, No. 4, pp. 831-834, Apr. 1985.

Hobart H. Willard, et al., *Instrumental Methods of Analysis*, Fifth Edition, D. Van Nostrand Company, New York, N.Y., pp. 647-656, 1974.

Frederick A. Lowenheim, *Electroplating*, McGraw-Hill Book Company, pp. 120 & 121, 1979.

* cited by examiner

- ◻ MEASURED AT 26 C
- ▲ MEASURED AT 26 C AFTER REF. ELECTRODE CALIBRATION
- ○ MEASURED AT 19 C

APPARATUS FOR CONTROLLING AND/OR MEASURING ADDITIVE CONCENTRATION IN AN ELECTROPLATING BATH

CROSS-REFERENCE TO RELATED APPLICATIONS

This application is a continuation of U.S. patent application Ser. No. 09/572,603, filed May 17, 2000 (now issued as U.S. Pat. No. 6,551,479), entitled "Apparatus for Controlling and/or Measuring Additive Concentration in an Electroplating Bath", which is a divisional of U.S. Patent application Ser. No. 09/387,084, entitled "Methods and Apparatus Controlling and/or Measuring Additive Concentration in an Electroplating Bath", filed Aug. 31, 1999, (now issued as U.S. Pat. No. 6,356,033) which is a continuation of International Application No. PCT/US99/09659, entitled "Methods and Apparatus for Controlling and/or Measuring Additive Concentration in an Electroplating Bath", filed May 3, 1999 and published in English under PCT Article 21(2), which claims priority from U.S. Provisional Patent Application Ser. No. 60/083,882, filed May 1, 1998, entitled "Closed Loop Electrolyte Composition Monitoring and Control System for Copper Interconnect Applications." The disclosures of these applications are incorporated herein by reference in their entireties.

STATEMENT REGARDING FEDERALLY SPONSORED RESEARCH OR DEVELOPMENT

Not Applicable

BACKGROUND OF THE INVENTION

The phenomenal growth exhibited by the semiconductor industry over the past three decades has been due in large part to the ability of manufacturers to provide a 25-30% per year cost reduction per function throughout this period. Design innovation, device architecture 'shrinks', wafer size increases, and yield improvement have been some of the factors enabling this remarkable performance. According to the 1997 Edition of the National Technology Roadmap for Semiconductors (NTRS), published by the Semiconductor Industry Association, the largest contribution to productivity growth over the next three device generations will be decreased feature size; this dimensional scaling increases the packing density of transistors per square centimeter in an integrated circuit.

Complexity of integrated circuits and resulting manufacturing challenges escalate as feature sizes decrease. Use of conventional materials technologies and design approaches arm projected to increase manufacturing complexity to the point where the costs of fabrication or deleterious effects on yield and reliability offset the benefits of dimensional scaling.

Among the most significant factors in determining device size and chip performance for the next technology generations, with transistor gate sizes starting at approximately 180 nm and diminishing to sub-100 nm widths, are the structures and materials employed for signal transmission to and from the active device regions. Globally referred to as 'interconnect', these processes already represent more than half the fabrication process budget for leading-edge microprocessors. Interconnect architecture improvements now rank among the most intense areas of semiconductor process and integration development, and are anticipated to remain so for the foreseeable future.

One of the enhancements to interconnect structures anticipated to see rapid adoption is the replacement of aluminum and tungsten signal transmission lines by lower-resistance copper. In a departure from conventional practice, where metals are typically vacuum deposited by sputtering or heterogeneous vapor/solid biphase reactions, copper interconnect will likely be introduced using electroplating or electrochemical deposition (ECD) processes, which feasibility studies have shown to be well matched to the demands of Damascene processes, the processes that have now been adopted by the microelectronic fabrication industry to form copper interconnects.

Though electroplating has long been employed as a fundamental step in fabrication of multilevel printed circuit boards, application of electroplating to fill sub-micron interconnect features is relatively recent and poses further additional problems, including the need for more stringent control of electroplating bath composition.

Electroplating is a complex process involving multiple ingredients in the plating bath. It is important that the concentration of several of the ingredients be kept within close tolerances in order to obtain a high quality deposit. In some cases, chemical analysis of individual solution constituents can be made regularly (such as pH measurement for acid content), and additions made as required. However, other addition agents such as brighteners, leveling agents, suppressants, etc., together with impurities, cannot be individually analyzed on an economical or timely basis by a commercial plating shop. Their operating concentration is low and their quantitative analysis is complicated and subject to error.

When using an electroplating bath, the ability to monitor and control bath composition is a key factor in ensuring uniform and reproducible deposit properties. In semiconductor and microelectronic component applications, the electronic and morphological properties of the copper films are of principal importance in determining final device performance and reliability. The stability of later processes in the Damascene patterning flow depend on repeatable mechanical properties including modulus, ductility, hardness, and surface texture. All of these deposit properties are controlled or strongly influenced by the composition of the electroplating bath.

Of particular importance is measurement and control of proprietary organic compounds which serve to modify the deposit properties through adsorption onto and desorption from the cathode surface during plating, affecting the diffusion rate of copper cations to nucleation and growth sites. These compounds are typically delivered as multi-component packages from plating chemistry vendors. One of the most important functions of the additive packages is to influence the throwing power of the electroplating bath: the relative insensitivity of plating rate to variations in cathodic current density across the wafer or in the vicinity of surface irregularities. The throwing power of the electrolyte has a major effect on the cross-wafer uniformity of plated film thickness and the success with which ultrafine trenches and vias (holes) are filled without included seams or voids. Organic additives have also been shown to have dramatic effects on mechanical film properties. Detection and quantification of these important bath constituents is complicated by the fact that they are effective at very low concentrations in the electrolyte, at several ppm or less.

Plating bath analysis for microelectronic applications is strongly driven by the need to limit variability and maintain device yields through maintenance of optimized process parameters. One method for controlling such ingredients in an electroplating bath is to make regular additions of particular ingredients based upon empirical rules established by experience. However, depletion of particular ingredients is not always constant with time or with bath use. Consequently, the concentration of the ingredients is not actually known and the level in the bath eventually diminishes or increases to a level where it is out of the acceptable range tolerance. If the additive content goes too far out of range, the quality of the metal deposit suffers and the deposit may be dull in appearance and/or brittle or powdery in structure. Other possible consequences include low throwing power and/or plating folds with bad leveling.

A common method for evaluating the quality of an electroplating bath is disclosed in Tench U.S. Pat. No. 4,132,605 (hereafter the Tench patent). In accordance with the procedures of the Tench patent, the potential of a working electrode 10 is swept through a voltammetric cycle, including a metal plating range and a metal stripping range, for at least two baths of known plating quality and an additional bath whose quality or concentration of brightener is to be evaluated. The integrated or peak current utilized during the metal stripping range is correlated with the quality of the bath of known quality. The integrated or peak current utilized to strip the metal in the bath of unknown quality is compared to the correlation and its quality evaluated. In a preferred embodiment of said patent, the potential of an inert working electrode 10 is swept by a function generator through the voltammetric cycle. An auxiliary electrode 20 immersed in the plating bath is coupled in series with a function generator and a coulometer to measure the charge from the working electrode 10 during the stripping portion of the cycle.

An improvement to the method disclosed in the Tench patent is described by Tench and White, in the *J. Electrochem. Soc.*, "Electrochemical Science and Technology", April, 1985, pp. 831-834 (hereafter the Tench publication). In accordance with the Tench publication, contaminant buildup in the copper plating bath affects the copper deposition rate and thus interferes with brightener analysis. The Tench publication teaches that rather than continuous sweep cycle utilized in the above-referenced patent, a method be used involving sequentially pulsing the electrode between appropriate metal plating, metal stripping, cleaning, and equilibrium potentials whereby the electrode surface is maintained in a clean and reproducible state. Stated otherwise, where the process of the Tench patent involves a continuous voltammetric sweep between about −600 mV and +1,000 mV versus a working electrode and back over a period of about 1 minute, the Tench publication pulses the potential, for example at −250 mV for 2 seconds to plate, +200 mV for a time sufficient to strip, +1,600 mV to clean for seconds, +425 mV for 5 seconds to equilibrate, all potentials referenced to a saturated Calomel electrode, after which the cycle is repeated until the difference between successive results are within a predetermined value, for example, within 2% of one another.

The procedure of the Tench publication provides some improvement over the procedure of the Tench patent, but during continuous use of an electroplating bath and following successive analysis, contaminants build up on the electrodes and analysis sensitivity is lost. Further, as the present inventor has found, such procedures frequently fail when applied to certain used baths. The inability to accurately measure additive concentrations in such used baths effectively reduces the life time of the bath and increases the cost associated with producing, for example, semiconductor integrated circuits and microelectronic components.

BRIEF SUMMARY OF THE INVENTION

A method for measuring a target constituent of an electroplating solution using an electroanalytical technique is set forth in which the electroplating solution includes one or more constituents whose by-products skew an initial electrical response to an energy input of the electroanalytical technique. The method comprises a first step in which an electroanalytical measurement cycle of the target constituent is initiated by providing an energy input to a pair of electrodes disposed in the electroplating solution. The energy input to the pair of electrodes is provided for at least a predetermined time period corresponding to a time period in which the electroanalytical measurement cycle reaches a steady-state condition. In a subsequent step, an electroanalytical measurement of the energy output of the electroanalytical technique is taken after the electroanalytical measurement cycle has reached the steady-state condition. The electroanalytical measurement is then used to determine an amount of the target constituent in the electroplating solution. An automatic dosing system that includes the foregoing method and/or one or more known electroanalytical techniques in a close-loop system is also set forth.

DETAILED DESCRIPTION OF THE INVENTION

In order to comprehend the present invention, an understanding of the various techniques suitable for analyzing an electroplating bath is helpful. To this end, a description of certain electroplating bath analysis techniques are set forth along with several problems with these techniques that have been identified and addressed by the inventors.

A major category of instrumental analysis suitable for monitoring an electroplating bath is electroanalysis. The electroanalytical methods use electrically conductive probes, called electrodes, to make electrical contact with the electroplating solution. The electrodes are used in conjunction with electric or electronic devices to which they are attached to measure an electrical parameter of the electroplating solution. The measured parameter is related to the type and quantity of additives in the electroplating solution.

Faradaic electroanalysis is attractive as an investigative analytical method principally because what is studied is the electrochemical activity of the bath sample under applied electrical stimulus; the measured responses are related in a fundamental way to the properties which influence the quality of the metal deposition process itself. Electroanalysis further offers the opportunity to study the mechanisms and kinetics of the plating process, and the influences the various bath components exert on plating rate suppression and acceleration.

Figure 1:
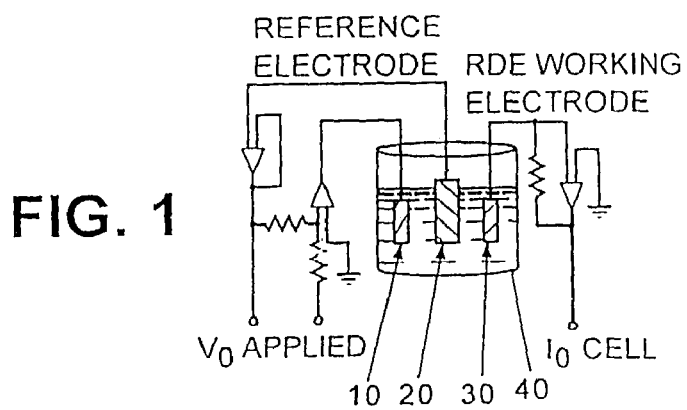
FIG. 1 is a diagram of an exemplary analytical cell used to implement an electroanalytical measurement of a an electroplating bath constituents.

Generally stated, electroanalytical methods are divided into categories according to the electric parameters that are measured. The major electroanalytical methods include potentiometry, amperometry, conductometry, voltammetry (and polarography), and coulometry. The names of the methods reflect the measured electric property or its units. Potentiometry measures electric potential (or voltage) while maintaining a constant (normally nearly zero) electric current between the electrodes. Amperometry monitors electric current (amperes). Conductometry measures conductance (the ability of a solution to carry an electric current). Voltammetry is a technique in which the potential is varied in a regular manner while the current is monitored. Polarography is a subtype of voltammetry that utilizes a liquid metal electrode. Coulometry is a method that monitors the quantity of electricity (coulombs) that are consumed during an electrochemical reaction involving the analyte. As will become apparent, the present invention is suitable for use in connection with all of these electroanalytical methods. The Voltammetry (or amperometry) involves the investigation of the current which develops in an electrochemical cell as a consequence of applied potential between a working and auxiliary electrode pair, with the potential measured against a suitable reference electrode. FIG. 1 shows the schematic wiring diagram for a device useful in practicing the present invention. Three electrodes, a working electrode 10, auxiliary electrode 20, and a reference electrode 30, are immersed in a bath cell 40. The reference electrode 30 may be, for example, be a Ag/AgCl double junction or Saturated Calomel Electrode (SCE). The working electrode 10, for example, may be one of several types, including the dropping mercury electrode (DME), hanging mercury drop electrode (HMDE), mercury thin film electrodes (MTFE), or an inert electrode which may be either stationary or of a rotating disc electrode (RDE) configuration. While the mercury-based electrodes offer the advantage of a surface that can be periodically 'renewed' to offer immunity to drift in electrochemical responses associated with changes in surface conditions (e.g., deposit build-up or smutting), inert RDE-type working electrodes with Pt, Pd, Ir, or Rh surfaces are most often employed in systems dedicated to plating bath analysis for convenience of system set-up, maintenance, and waste handling. FIG. 1 illustrates use of an RDE-type electrode in which relative motion between the working electrode 10 and the bath is established by a motor (5) that rotates the working electrode 10. Electrical contact to the working electrode 10 is made by, for example, slip brushes. Voltammetric cycles can be specified to provide in-situ cleaning of the RDE surface, and analytical methods are known which minimize the influence of slight changes in the electrode surface state over time. Potentiometry is conducted in identical apparatus, with evaluation of the voltage between the working and auxiliary electrodes required to maintain a forced current.

A computer (6) is used to control an electronic potentiostat (7) which controls the energy input between the working electrode 10 and the reference electrode 30. For laboratory testing of the method, instrumentation such as a Pine Instruments potentiostat under IBM computer control may be used. Using a suitable program, the energy input sequences may be applied to the working electrode 10. The output of the device can also be plotted on an X-Y recorder to graphically display the changes in energy output versus time for each step. The terms "energy input" and "energy output" in the following description of the methods will refer to control of the potential (energy input) while monitoring current density (energy output), or control of current density (energy input) while monitoring potential (energy output).

The most widely applied electroanalytical technique for plating bath analysis is stripping voltammetry, with Cyclic Voltammetric Stripping (CVS) or a closely related variant, Cyclic Pulsed Voltammetric Stripping (CPVS) representing common methods. Both techniques depend on controlling the voltage between the working electrode 10 and auxiliary electrode 20 with the potentiostat such that the working electrode 10 is cycled between cathodic and anodic potentials while in contact with the electroplating solution. A metal film is alternately reduced on the working electrode 10 surface and subsequently stripped by anodic dissolution. The potentiostat cycle is defined so that the current can be integrated over time during the stripping period, allowing quantification of the electric charge in coulombs transferred during the time required for complete film dissolution. The charge is directly related to the molar quantity of metal stripped (and therefore to the amount initially deposited) by Faraday's laws. The stripping charge is monitored rather than the charge transferred during film deposition because the stripping charge is less sensitive to changing electrode surface state and less influenced by factors such as charging and impurity currents. Empirically, too, there are inherent advantages of monitoring a process which proceeds to a well-defined endpoint.

The current/voltage/time relationship during analysis is extremely sensitive to variations in electroplating bath composition and, not incidentally, measurement conditions such as temperature. If sufficient care is taken in methods development and measurement technique—if, for instance, all component concentrations other than the one of interest can be held relatively constant—then stripping voltammetry can be employed to generate calibration curves with which subsequent analyses can be compared to yield reasonably accurate quantification of analyte composition.

Figure 2:
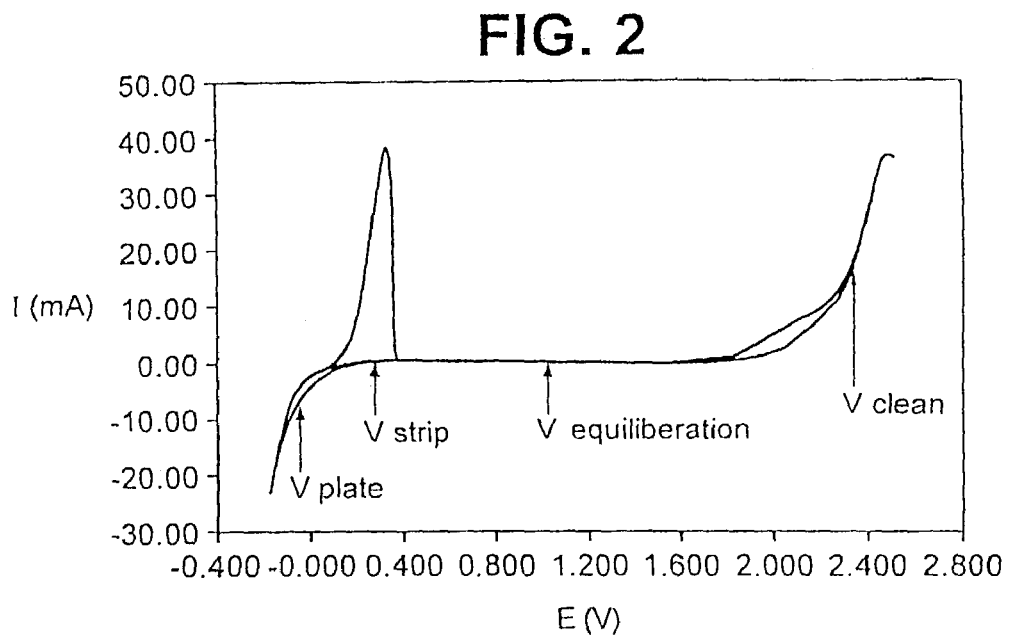
FIGS. 2 and 3 are graphs illustrating the implementation of a CVS measurement process.

In CVS analysis, the potential between the working electrode 10 and auxiliary electrode 20 is swept at a constant rate between user-defined limits. The voltage sweep may be repeated several times per analysis cycle, with the working electrode 10 alternating between film deposition and stripping, until a repeatable current vs. voltage response is obtained. The plot showing current as the dependent variable over the traversed potential range is termed a voltammogram, and provides a kind of 'fingerprint' of the electrochemical response of the electroplating bath. An example of a voltammogram for an acid copper electrolyte of specific composition is shown as FIG. 2, with the regions associated with metal film deposition and stripping noted. Because the potential sweep rate is held constant during analysis the area of the current peak associated with stripping is proportional to the stripping charge and, therefore, to variation in the electrolyte composition.

Figure 3:
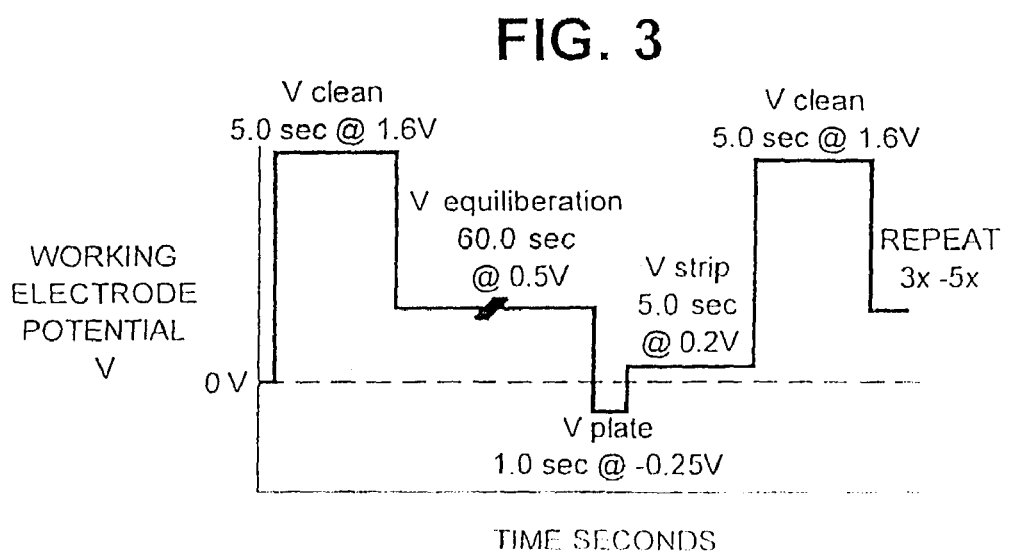

CPVS differs in that the potential between working electrode 10 and auxiliary electrode 20 is not swept over a range at a constant rate, but rather stepped between discrete values while the pulse width at each voltage is either held to fixed times (e.g., during deposition) or maintained until endpoint is achieved (during stripping). A typical process sequence for CPVS analysis is shown in FIG. 3. The working electrode 10 is first cleaned at a high anodic potential ($V_{clean}$) for a few seconds, followed by a few seconds at $V_{equiliberation}$. Metal is deposited on the electrode surface during a cathodic pulse $V_{plate}$ then anodically dissolved at $V_{strip}$ until all the metal is removed (i.e., stripping current is extinguished).

The integration of the current during the stripping pulse of the cycle yields a measure of charge, which as before is directly proportional to the moles of film deposited atvplaw. With sufficiently precise control of the deposition pulse width, the amount of metal deposited (and subsequently stripped at $V_{strip}$ can be correlated through calibration to the makeup of the electrolyte.

Although the voltametric stripping techniques are of potential utility in quantitating a number of plating bath components, in practice they are most often employed for evaluating levels of organic additives such as suppressing and brightening agents. A number of calibration methods have been proposed for developing correlations between stripping charges and concentration of plating bath species; several have reportedly been put into practice with good results.

The present inventors have recognized that one of the most problematic shortcomings of voltammetric analyses are their sensitivities to so-called 'matrix effects'. Many plating bath components and their breakdown products can display convoluted electrochemical interactions, hence the stripping charge responses can be ambiguous if several constituents have undergone significant concentration change simultaneously.

Figure 4:
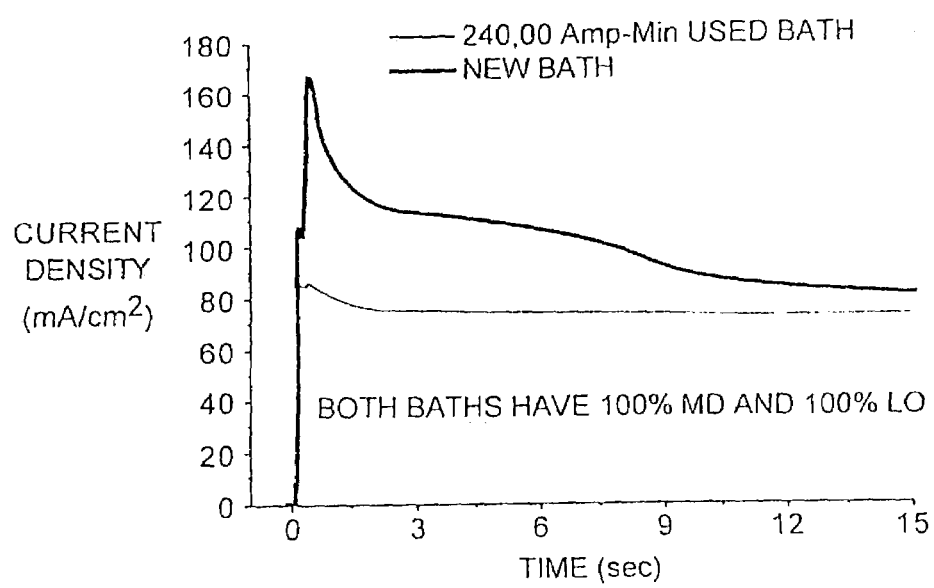
FIG. 4 is a graph illustrating the differences in the electrical response of a new electroplating bath and an old electroplating bath.

With respect to certain electroplating solutions (such as those available from Enthone-OMI), the present inventors have recognized that the organic component used as the brightener is consumed and breaks down into reaction by-products. As measured using the CVS technique, either these by-products or excess surfactant (which builds up with time) act as a pseudo-suppressor. The buildup of pseudo-suppressor introduces substantial errors in the CVS analysis whereby an excess amount of suppressor is indicated. As the present inventors have found, the reason for this erroneous result from CVS is that the used bath responds differently than a new bath for the first 10-20 seconds of deposition. More particularly, the inventors have found that the current transient is suppressed. CVS interprets this as plating bath suppression because the CVS technique never reaches steady-state conditions. Rather, the normally used scan rate is 100 mV/sec giving a total metal deposition time of less than 5 seconds. FIG. 4 is a plot of a used and new bath with approximately the same amount of suppressor in each. Note that at a time of 5 seconds, the current exhibited by the used bath is much less than that of the new bath. This difference is mistakenly measured by the CVS method as extra suppressor.

From the foregoing analysis, the present inventors have recognized that, as steady-state conditions are approached (e.g., at t=15 seconds), the two currents approach the same value. Based on this recognition, a new method is set forth that correctly eliminates the error due to this current transient suppression. The method can measure suppressor in used electroplating baths as well as new electroplating baths thereby facilitating use of the electroplating bath for an extended period of time since the components (e.g., suppressor) may be accurately measured and dosed during this extended period of time unlike in prior additive measurement techniques.

Generally stated, the inventive analysis techniques set forth herein modify existing techniques so that the analytical measurements are taken as the particular technique achieves or approaches a steady-state condition. Examples of such techniques include, but are not limited to the following:
1. Chronoamperometry;
2. Chronopotentiometry;
3. Cyclic Voltammetry Stripping (CVS) where the scan rate is substantially reduced so as to approach steady-state;
4. CVS with a pause in the plating region so as to approach steady state;
5. Multiple or single linear sweeps that are performed at a slows rate and then calibrated versus organic concentration; and
6. Cyclic Pulse Voltammetry Stripping where the plating time is increases so as to approach steady-state.

Although any of the foregoing analysis techniques are suitable for use in accordance with the teachings of the present invention, the following discussion will center on a specific embodiment of the technique using chronoamperometry (CA) measurements. The advantage of the CA technique over the known CVS technique is the fact that it measures at steady-state.

Suppressor analysis using chronoamperometry can be performed using a series of basic steps, some of which are optional, including:
1. Generating a CA analysis calibration curve (optional);
2. Performing CA analysis on a bath sample (repeats with dilution & titration, as will be set forth below, are optional);
3. Using the data obtained in steps 1 and 2 to mathematically calculate the rate of suppression (optional); and
4. Calculating the amount of suppression using a user defined logic routine.

A preferred manner of executing the chronoamperometry includes the following

| STEP NUMBER | ENERGY INPUT | DESCRIPTION |
| --- | --- | --- |
| 1 | 1.6 V for 5 seconds | high oxidation step |
| 2 | 0.5 V for 150 seconds | seed electrode with copper |
| 3 | −0.1 V for 30 sec | low oxidation step/stabilize electrode |
| 4 | +0.062 V for 15 sec | establish equilibrium @ OCP ≈ +0.062 V |
| 5 | CA @ −0.25 V for 60 seconds | measure the current after about 60 seconds have elapsed |

The potentials listed are relative to a Ag—AgCl electrode.

Figure 5:
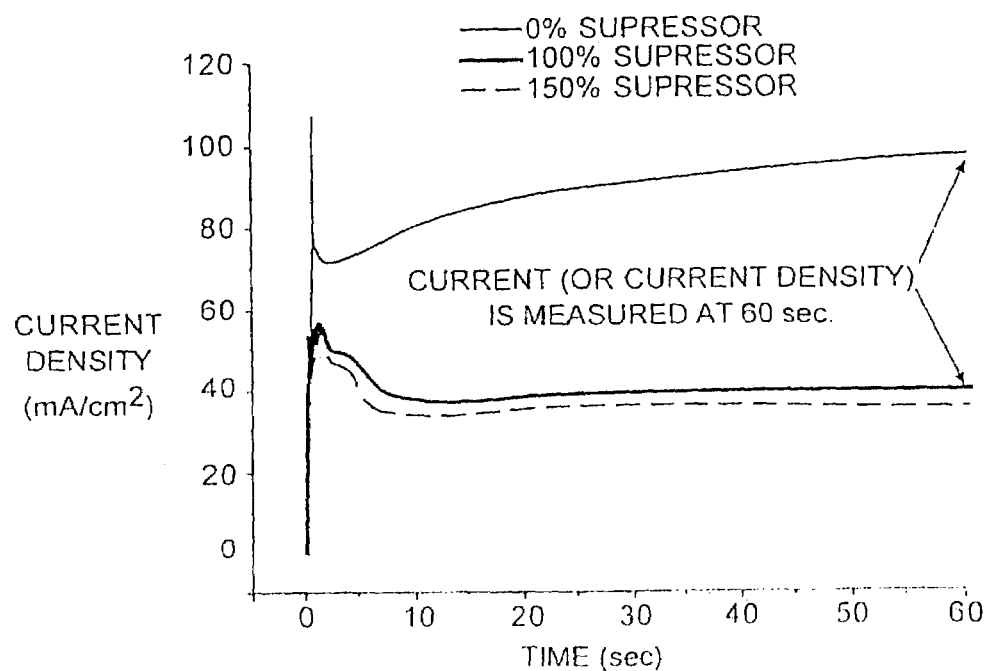
FIG. 5 is a graph illustrating an electroanalytical measurement taken in accordance with one embodiment of the present invention.

An example CA analysis is shown in FIG. 5 where the measured parameter is current at a user specified time. For the examples disclosed herein, the current is measured at about 60 seconds.

Figure 6:
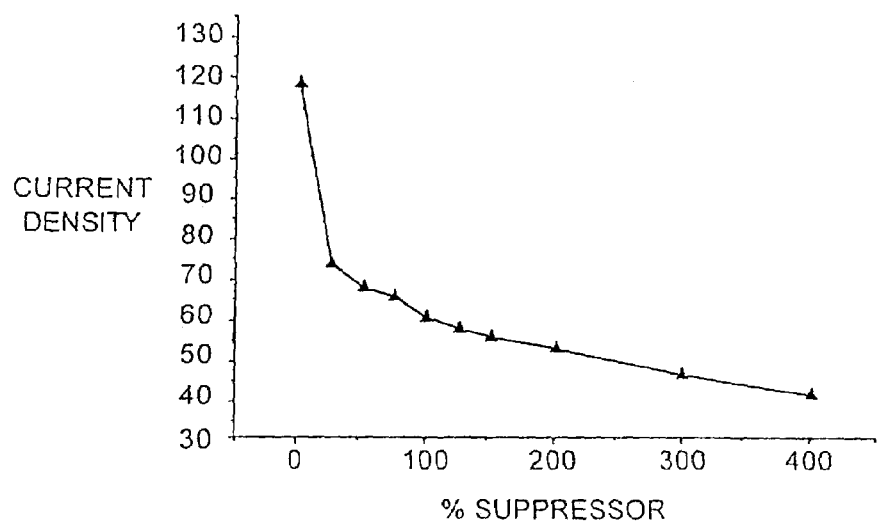
FIG. 6 is an exemplary calibration graph that may be used to determine the concentration of an electroplating bath constituent, such as a suppressor, based on a measurement such as the one taken in FIG. 5.

The calibration curve mentioned in step 1 above comprises a series of CA plots of known concentration where the measurable is plotted as a function of concentration as shown in FIG. 6. While this method may be used to correlate suppressor concentration versus current, it is important to keep variables such as temperature, reference electrode calibration, etc. constant to reduce errors. Potential errors induced by such variables are illustrated in FIG. 7.

Figure 7:
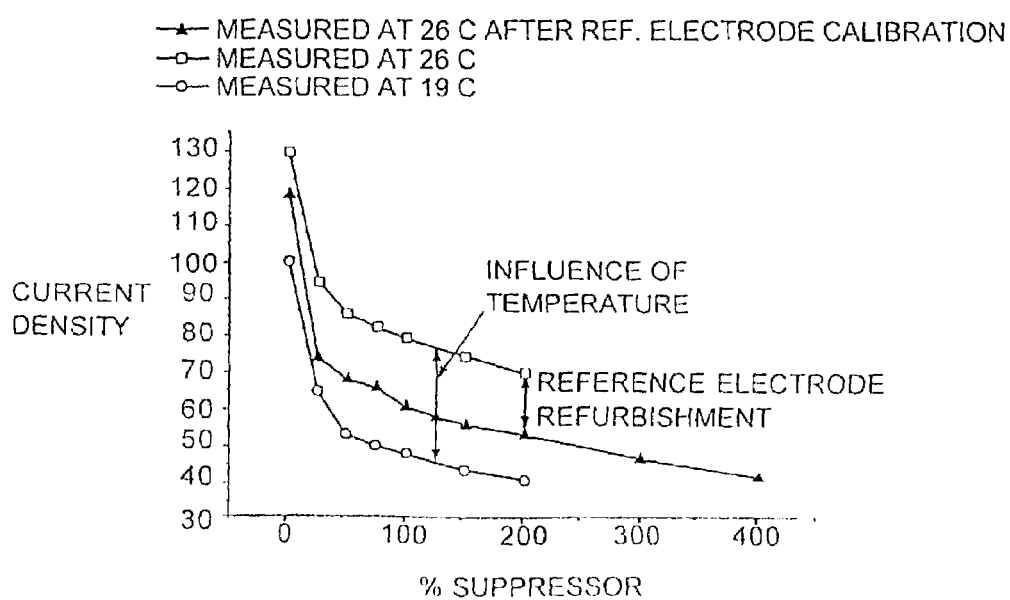
FIG. 7 is a graph illustrating the effect of different variables on measurements taken during an electroanalytical measurement process.
Figure 8:
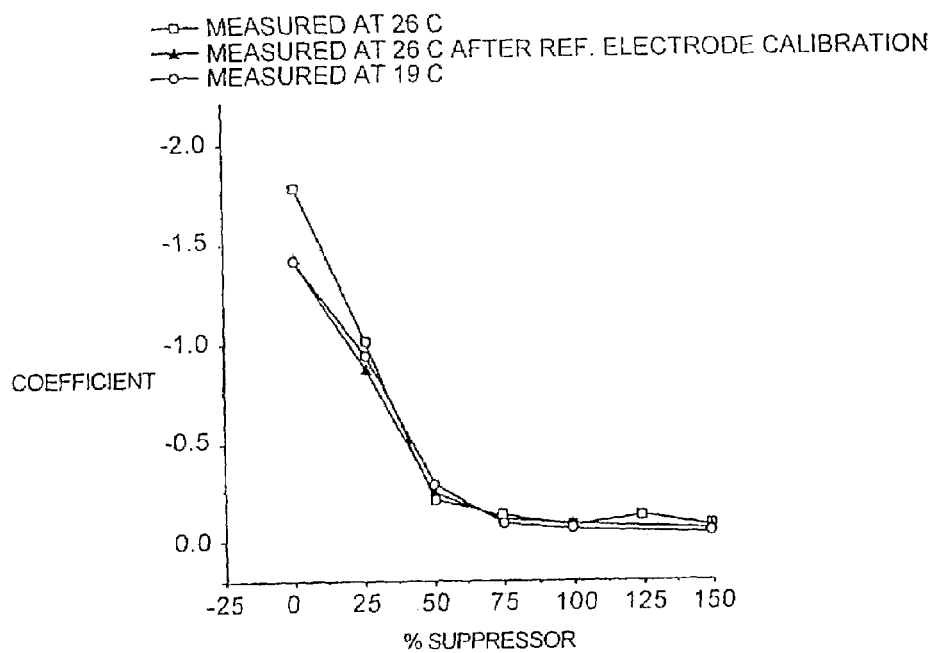
FIG. 8 is a graph illustrating a normalized curve based on the data of FIG. 7 that assists in reducing the effect of the different variables on the measurement data.

The optional next step is to mathematically calculate the rate of suppression by taking the $1^{st}$ derivative of the data shown in FIG. 7. This calculated data is shown in FIG. 8 and has the advantage of minimizing the influences of variables such as temperature and electrode calibration.

The final step is to relate the data taken and/or take data in such a way so that the amount of suppressor in the bath can be calculated. Six methods are set forth herein to accomplish this task using chronoamperometry. They are:

I. Use no titration—relate current or some aspect of the CA plot to a calibration curve;
II. Concentration titration using the unknown bath as the diluent and suppressor as the titrant;
III. Concentration titration using diluted unknown bath as the diluent and suppressor as the titrant;
IV. Concentration titration using Virgin Make-Up solution (VMS) as the diluent and the unknown bath as the titrant;
V. Concentration titration using linear slope analysis and suppressor or plating bath as the titrant and VMS or plating bath as the diluent; and
VI. Dilution Titration using the undiluted, unknown bath as the diluent and VMS (with or without carrier) as the titrant.

In the foregoing descriptions, the term "concentration titration" refers to a method that measures a response in an electroplating bath with increasing concentration of the suppressor, and the term "dilution titration" refers to a method that measures a response with decreasing suppressor concentration. Exemplary steps for executing these methods using, for example, an Enthone based chemistry, are described below. These exemplary steps or "recipes" are illustrative and further steps may be added (e.g., for electrode conditioning) as required, chemical volumes may be changed, etc. Also, it will be recognized that the following methods may be combined with one another.

Exemplary Method I

In accordance with the first exemplary method in which no titration is used, current or some other aspect of the CA plot is related to a calibration curve. To this end, the following process steps may be implemented:

1. Remove an amount of electroplating bath (i.e., 50 mls) from the electroplating reactor;
2. Perform a CA measurement using the electroplating bath removed in Step 1, ensuring that the measurement is taken during the CA process as it approaches or reaches a steady-state (e.g., by using the preferred process steps set forth above);
3. Compare the resulting measurement with the calibration curve to determine the amount of additive (i.e., suppressant) in the bath.

Exemplary Method I is advantageous in that it is a very simple process to implement. However, a disadvantage of this approach is the fact that it requires a predetermined calibration curve.

Exemplary Method II

The second exemplary method involves concentration titration using the unknown bath as the diluent and the suppressor as the titrant. To this end, the following process steps may be implemented:

1. Remove an amount of electroplating bath (i.e., 50 mls) from the electroplating reactor;
2. Perform a CA measurement using the electroplating bath removed in Step 1, ensuring that the measurement is taken during the CA process as it approaches or reaches a steady-state (e.g., by using the preferred process steps set forth above);
3. Add 5%-25% (0.0075-0.0375 mls) suppressor;
4. Perform a CA measurement using the solution formed in Step 3, ensuring that the measurement is taken during the CA process as it approaches or reaches a steady-state (e.g., by using the preferred process steps set forth above);
5. Repeat Steps 3 and 4 as necessary to generate a slope, or to otherwise gather enough data to answer a logic criteria (e.g., is the concentration below the "knee");
6. Compare the measurement results obtained during one or more cycles of Steps 3 and 4 to the calibration curve; and
7. Calculate the concentration based on the comparison made in Step 6.

One advantage of Exemplary Method II is that the titration does not require either AE carrier syringe or a VMS Syringe. However, it has been found that the accuracy of this method decreases at high initial suppressor concentrations. This is due to the fact that the slope decreases with this particular Enthone chemistry.

Exemplary Method III

The third exemplary method involves concentration titration using the diluted unknown bath as the diluent and suppressor as the titrant. To this end, the following process steps may be implemented:

1. Remove an amount of electroplating bath (i.e., 10 mls) from the electroplating reactor;
2. Add an amount of VMS (40 mls)+100% (0.4 mls) carrier to the amount of electroplating bath removed in Step 1;
3. Perform a CA measurement using the solution formed in Step 2, ensuring that the measurement is taken during the CA process as it approaches or reaches a steady-state (e.g., by using the preferred process steps set forth above);
4. Add 5%-25% (0.0075-0.0375 mls) suppressor;
5. Perform a CA measurement using the solution formed in Step 4, ensuring that the measurement is taken during the CA process as it approaches or reaches a steady-state (e.g., by using the preferred process steps set forth above);
6. Repeat Steps 4 and 5 as necessary to generate a slope, or to otherwise gather enough data to answer a logic criteria (e.g., is the concentration below the "knee");
7. Compare the measurement results obtained du ring one or more cycles of Steps 4 and 5 to the calibration curve; and
8. Calculate the concentration based on the comparison made in Step 7.

Exemplary Method III exhibits an increased accuracy over Exemplary Method II by diluting the electroplating bath sample to the more accurate end of the calibration curve Exemplary Method IV The fourth exemplary method involves concentration titration using Virgin Make-Up (VMS) as the diluent and the unknown bath as the titrant. To this end, the following process steps may be implemented:

1. Remove an amount of electroplating bath (i.e., 10 mls) from the electroplating reactor;
2. Mix a solution of VMS (40 mls)+100% (0.4 mls);
3. Perform a CA measurement using the solution formed in Step 2, ensuring that the measurement is taken during the CA process as it approaches or reaches a steady-state (e.g., by using the preferred process steps set forth above);

4. Add a quantity of the unknown bath removed in Step 1 (10-25% of the initial VMS volume (4-10 mls)) to VMS;
5. Perform a CA measurement using the solution formed in Step 4, ensuring that the measurement is taken during the CA process as it approaches or reaches a steady-state (e.g., by using the preferred process steps set forth above);
6. Repeat Steps 4 and 5 until a sufficient curve is generated;
7. Compare the curve generated in Steps 4-6 to a calibration curve to calculate Calculate the constituent concentration.

It should be noted that the accuracy of Exemplary Method IV will decrease significantly if the bath solution is too dilute Exemplary Method V The fifth exemplary method involves concentration titration using linear slope analysis. To this end, the following process steps may be implemented:
1. Remove an amount of electroplating bath (i.e., 10 mls) from the electroplating reactor;
2. Provide a solution of VMS (50 mls)+100% (0.5 mls);
3. Perform a CA measurement using the solution formed in Step 2, ensuring that the measurement is taken during the CA process as it approaches or reaches a steady-state (e.g., by using the preferred process steps set forth above);
4. Add an amount of the electroplating bath removed in Step 1 to the solution formed in Step 2;
5. Perform a CA measurement using the solution formed in Step 4, ensuring that the measurement is taken during the CA process as it approaches or reaches a steady-state (e.g., by using the preferred process steps set forth above);
6. Add 10-25% suppressor to the solution (0.015-0.037 mls);
7. Perform a CA measurement using the solution formed in Step 6, ensuring that the measurement is taken during the CA process as it approaches or reaches a steady-state (e.g., by using the preferred process steps set forth above);
8. Repeat Steps 6 and 7 to generate a measurement curve; and
9. Using a linear fit or other appropriate curve, calculate the amount of the suppressor in the unknown electroplating bath.

This exemplary method works well in those instances in which a linear region may be obtained. Additionally, it does not require a calibration curve and, further, is less dependent on bath carrier solution than the foregoing exemplary methods.

Exemplary Method VI

The sixth exemplary method involves dilution titration and comprises performing a CA test on the unknown bath, dividing the unknown bath by diluting it with Virgin Make-Up Solution (VMS), performing another CA test, comparing the measurable with a logic criteria (e.g., matching the calibration curve or until a specific delta change has occurred, etc.). To this end, the following process steps may be implemented:
1. Remove an amount of electroplating bath (i.e., 40 mls) from the electroplating reactor;
2. Perform a CA measurement using the solution formed in Step 1, ensuring that the measurement is taken during the CA process as it approaches or reaches a steady-state (e.g., by using the preferred process steps set forth above);
3. Add 10-20% (4-8 mls) of the VMS plus corresponding carrier (0.04-0.08 mls) to the unknown electroplating bath removed in Step 1;
4. Perform a CA measurement using the solution formed in Step 3, ensuring that the measurement is taken during the CA process as it approaches or reaches a steady-state (e.g., by using the preferred process steps set forth above);
5. Calculate the slope of the measurement taken in Steps 2 and 4;
6. Compare with a logic criteria (e.g., compare the slope with the calibration curve);
7. Repeat steps 3-5 on the same sample until the degree of resolution is achieved.

Exemplary Method VI is advantageous in that it is relatively easy to implement. Further, the method can be repeated until the sensitive range of the calibration curve is reached thereby providing for a wide range of measurement sensitivity and resolution.

Automatic Dosing System

As the microelectronics fabrication industry moves toward widespread use of electroplating, particularly of micro-structures, there is an increased need for highly accurate dosing systems that replenish the various components of the electroplating bath. To this end, dosing systems have been developed for use with electroplating tools that are used at microelectronic fabrication facilities. Most known systems, however, execute the dosing function using open-loop, predetermined models that replenish the electroplating bath constituents based on emperically determined data. Such systems may be suitable for certain electroplating processes, but become less viable as new device requirements impose more rigorous standards on the make-up of the electroplating bath.

Figure 9:
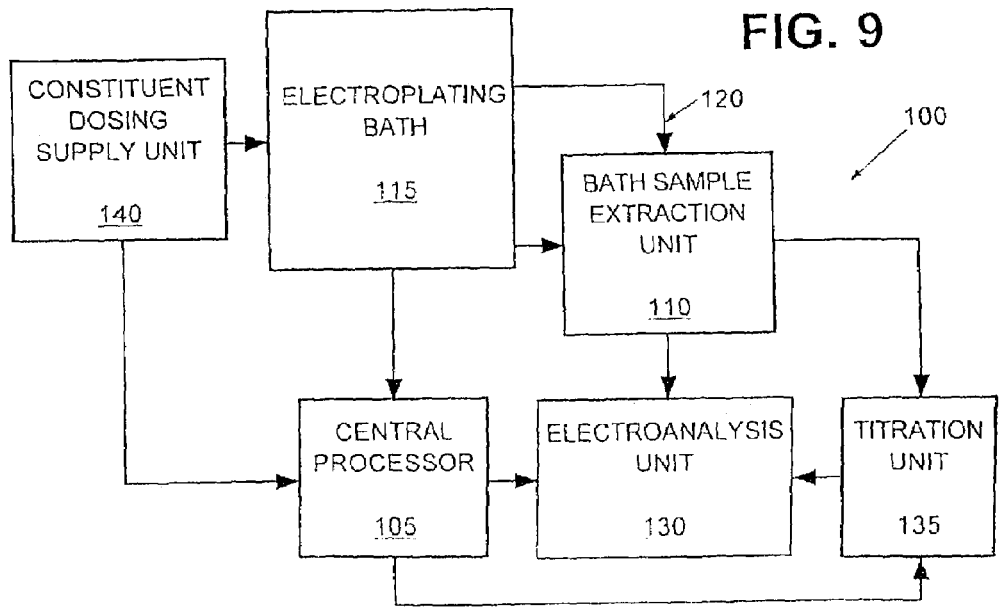
FIG. 9 is a schematic block diagram of one embodiment of a dosing system that uses an electroanalytical technique as part of a feedback process to replenish an electroplating bath with a target constituent.

More accurate control both the plating bath constituents may be obtained using a dosing system that employs measurement feedback to ascertain the proper quantity of a bath constituents. An exemplary feedback dosing system is illustrated in FIG. 9. As shown, the dosing system, shown generally at 100, includes a central processor 105 that is used to control the operations necessary to perform the following functions: 1) extract a sample of the electroplating bath that is to be analyzed; 2) execute an electroanalytical technique on the electroplating bath sample; 3) calculate the amount of the electroplating bath constituent present in the sample based on the results of the electroanalytical technique; and 4) use the resulting calculation to automatically control the supply of an amount of the constituent to replenish the electroplating bath, raising the constituent concentration to a predetermined level.

In order to execute the foregoing functions, the central processor 105 is connected to interact with and exchange information with a number of units and systems. A bath sample extraction unit 110 is connected for control by the central processor 105. The bath sample extraction unit 110 is connected to receive electroplating solution along line 120 from the principal electroplating bath 115 in response to control signals/commands received from the central processor 105 along communication link 125. In response to such control signals/commands, the bath sample extraction unit 110 provides the bath sample to either an electroanalysis unit 130 or to an optional titration system 135.

Both the electroanalysis unit 130 and the optional titration system 135 are under the control of the central processor 105. The central processor 105 coordinates the activities of the electroanalysis unit 130 and titration system 135 to execute the desired electroanalytical technique. The electroanalytical technique can be any of the known techniques, or can be one or more of the inventive techniques disclosed herein.

The central processor 105 that acquires the requisite data based on the electroanalytical technique to directly calculate or otherwise determine in a relative manner the concentration of the plating bath constituent. Based on this calculation/determination, the central processor 105 directs one or more constituent dosing supply units 140 to provide the necessary amount of the constituent (or amount of solution containing the constituent) to the electroplating bath 115, thus completing the feedback control process.

It will be recognized that the inventive electroanalytical techniques described above can be implemented in a manual, semi-automatic, or completely automatic manner. Dosing system 100 is merely provided as an illustrative, yet novel manner in which to implement one or more known and/or inventive electroanalytical techniques described above.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. A system for maintaining a concentration level of a target constituent of an electroplating bath comprising:
    a sample extraction unit connected to automatically remove a sample of the electroplating bath;
    an electroanalysis unit connected to receive and perform an electroanalytical technique on the sample obtained by the sample extraction unit, wherein the electroanalytical technique includes at least one of a plating measurement cycle that plates a metal on an electrode of the electroanalysis unit and a stripping measurement cycle that strips the metal from the electrode, and wherein the entire sample is retained within the electroanalysis unit during performance of the electroanalytical technique;
    a constituent dosing supply unit connected to provide an amount of the target constituent to the electroplating bath; and
    a programmable control unit connected to communicate with:
        (a) the sample extraction unit to control extraction of the sample from the electroplating bath and supply of the sample to the electroanalysis unit;
        (b) the electroanalysis unit to execute the electroanalytical technique to determine an amount of the target constituent in the sample; and
        (c) the constituent dosing supply unit to control the amount of the target constituent provided to the electroplating bath based on the amount of the target constituent measured in the sample through the use of the electroanalytical technique.

2. The system of claim 1, wherein the electroanalytical technique performed by the electroanalysis unit includes a method selected from the group consisting of chronopotentiometry and chronoamperometry.

3. The system of claim 1, wherein the electroanalytical technique performed by the electroanalysis unit includes a method selected from the group consisting of cyclic voltammetric stripping and cyclic voltammetric pulsed stripping.

4. The system of claim 1 further comprising:
    a titration unit connected to deliver a titrant to the electroanalysis unit, the titration unit being further connected to communicate with the programmable control unit to facilitate delivery of a selected amount of the titrant into the electroanalysis unit at selected time intervals during system operation.

5. The system of claim 4, wherein the titration unit is further connected to the sample extraction unit, and the selected amount of the titrant includes a portion of the sample removed by the sample extraction unit.

6. The system of claim 4, wherein the titrant includes a predetermined amount of the target constituent.

7. The system of claim 1 wherein the system is configured to selectively provide the sample removed from the electroplating bath to the electroanalysis unit such that the sample received by the sample extraction unit has substantially the same chemical composition upon delivery to the electroanalysis unit.

8. The system of claim 1 wherein the electroanalysis unit is connected within the system to facilitate receipt of the sample directly from the sample extraction unit such that the sample has not been chemically and/or physically processed or altered prior to delivery to the electroanalysis unit.

9. An apparatus for maintaining a concentration level of a target constituent of an electroplating bath, said electroplating bath also including one or more additional constituents that during an initial time period at which an electroanalytical technique is applied skew an electroanalytical response to the electroanalytical technique, the apparatus comprising:
    a sample extraction unit connected to automatically remove a sample of the electroplating bath;
    an electroanalysis unit connected to receive the sample obtained by the sample extraction unit;
    a constituent dosing supply unit connected to provide an amount of the target constituent to the electroplating bath; and
    a programmable control unit in communication with the sample extraction unit, the electroanalysis unit and the constituent dosing supply unit, wherein the programmable control unit is configured to:
        (a) control the sample extraction unit to extract the sample from the electroplating bath and to supply the sample to the electroanalysis unit;
        (b) control execution of the electroanalytical technique by the electroanalysis unit for determination of an amount of the target constituent in the sample so as to ensure that an electroanalytical response output by the electroanalysis unit is measured at a selected time period during the execution of the electroanalytical technique, wherein the selected time period is after the initial time period has lapsed and at which skewing of the electroanalytical response by the one or more additional constituents is negligible; and
        (c) control the constituent dosing supply unit to provide a selected dosage of the target constituent to the electroplating bath based on the amount of the target constituent measured in the sample at the selected time period.

10. The system of claim 9, wherein the electroanalytical technique performed by the electroanalysis unit includes a method selected from the group consisting of chronopotentiometry and chronoamperometry.

11. The system of claim 9, wherein the electroanalytical technique performed by the electroanalysis unit includes a method selected from the group consisting of cyclic voltammetric stripping and cyclic voltammetric pulsed stripping.

12. A system for maintaining a concentration level of an organic target constituent of an electroplating bath comprising:
   an electroanalysis unit connected to perform an electroanalytical technique on a test solution to determine a concentration of the organic target constituent in the electroplating bath, wherein the entire test solution is retained within a single vessel during performance of the electroanalytical technique by the electroanalysis unit, and wherein the electroanalytical technique includes at least one of a plating measurement cycle that plates a metal on an electrode of the electroanalysis unit and a stripping measurement cycle that strips the metal from the electrode; and
   a control unit to control the amount of the organic target constituent in the electroplating bath based upon the concentration of the organic target constituent determined by the electroanalysis unit.

13. The system of claim 12, wherein the electroanalytical technique performed by the electroanalysis unit is one of chronoamperometry and chronopotentiometry.

14. The system of claim 12, wherein the electroanalytical technique performed by the electroanalysis unit is one of cyclic voltammetric stripping and cyclic pulsed voltammetric stripping.

15. The system of claim 12, wherein the system is configured to selectively facilitate performance of the electroanalytical technique by the electroanalysis unit with a liquid that has substantially the same chemical composition as the electroplating bath.

16. A method for real-time replenishment of depleted organics in an electrolyte solution, the method comprising:
   measuring a concentration of depleted organics in the electrolyte solution by performing a technique with a test solution that remains in a single vessel during performance of the technique, wherein the concentration measurement includes at least one of a plating measurement cycle that plates a metal on an electrode of the electroanalysis unit and a stripping measurement cycle that strips the metal from the electrode;
   transmitting the measured concentration to a system controller;
   determining a replenishment of organics corresponding to the measured concentration of depleted organics with the system controller; and
   replenishing organics into the electrolyte solution in accordance with the determined replenishment of organics.

17. The method of claim 16, wherein the concentration measurement is conducted via a CVS assembly.

18. The method of claim 16, wherein the system controller is configured to receive measurement inputs, calculate replenishment volumes, and control a replenishment device.

19. The method of claim 16, wherein no other concentration determination of the electrolyte solution is performed prior to the measuring the concentration of depleted organics in the electrolyte solution.

20. The method of claim 16, wherein the electrolyte solution has not been chemically and/or physically processed or altered prior to measuring the concentration of depleted organics in the electrolyte solution.

21. The method of claim 16, wherein the test solution comprises a sample extracted from the electrolyte solution.

22. A method for maintaining a concentration level of an organic target constituent in an electroplating bath, the method comprising:
   performing an electroanalytical technique on a test solution with an electroanalysis unit to determine a concentration of the organic target constituent in the electroplating bath, wherein the entire test solution is maintained within a single vessel during performance of the electroanalytical technique, and wherein the electroanalytical technique includes at least one of a plating measurement cycle that plates a metal on an electrode of the electroanalysis unit and a stripping measurement cycle that strips the metal from the electrode; and
   automatically controlling, via a control unit, the amount of the organic target constituent in the electroplating bath based upon the concentration of the organic target constituent determined by the electroanalysis unit.

23. The method of claim 22, wherein the electroanalytical technique performed by the electroanalysis unit is one of chronoamperometry and chronopotentiometry.

24. The method of claim 22, wherein the electroanalytical technique performed by the electroanalysis unit is one of cyclic voltammetric stripping and cyclic pulsed voltammetric stripping.

25. The method of claim 22, wherein no other concentration determination of the electroplating bath is performed prior to the electroanalytical technique performed by the electroanalysis unit.

26. The method of claim 22, wherein the electroanalytical technique is selectively performed by the electroanalysis unit with a solution that has substantially the same chemical composition as the electroplating bath.

27. The method of claim 22, wherein the test solution comprises a sample extracted from the electroplating bath.

28. A system for real-time replenishment of depleted organics in an electrolyte solution, the system comprising:
   an analysis unit configured to perform an electroanalytical technique on a test solution that determines a concentration of a depleted organic in the electrolyte solution, wherein the entire test solution is retained within a single vessel during performance of the technique by the analysis unit, and wherein the electroanalytical technique includes at least one of a plating measurement cycle that plates a metal on an electrode of the electroanalysis unit and a stripping measurement cycle that strips the metal from the electrode; and
   a control unit configured to:
      determine a replenishment of organics corresponding to the concentration of the depleted organic as determined by the analysis unit; and
      replenish organics into the electrolyte solution in accordance with the determined replenishment of organics.

29. The system of claim 28, wherein the electroanalytical technique performed by the electroanalysis unit includes a method selected from the group consisting of cyclic voltammetric stripping and cyclic voltammetric pulsed stripping.

30. The system of claim 28, wherein the test solution comprises a sample extracted from the electrolyte solution.

31. The system of claim 30, further comprising:
   a sample extraction unit connected to automatically extract the sample from the electrolyte solution for analysis by the analysis unit.

32. The system of claim 28, wherein the system is configured to direct the electrolyte solution to the analysis unit such that no other concentration determination of the electrolyte solution is performed prior to the analysis unit performing a technique that determines a concentration of a depleted organic in the electrolyte solution.

* * * * *